(12) United States Patent
Jamali

(10) Patent No.: US 12,350,175 B2
(45) Date of Patent: Jul. 8, 2025

(54) BONE CUTTING SYSTEM AND APPARATUS

(71) Applicant: Amir A Jamali, Oakland, CA (US)

(72) Inventor: Amir A Jamali, Oakland, CA (US)

(*) Notice: Subject to any disclaimer, the term of this patent is extended or adjusted under 35 U.S.C. 154(b) by 274 days.

(21) Appl. No.: 18/200,929

(22) Filed: May 23, 2023

(65) Prior Publication Data

US 2023/0372123 A1 Nov. 23, 2023

Related U.S. Application Data

(60) Provisional application No. 63/365,146, filed on May 23, 2022.

(51) Int. Cl.
*A61F 2/46* (2006.01)

(52) U.S. Cl.
CPC .... *A61F 2/4644* (2013.01); *A61F 2002/4649* (2013.01)

(58) Field of Classification Search
CPC .. A61F 2/46; A61F 2/4644; A61F 2002/4645; A61F 2002/4649
See application file for complete search history.

(56) References Cited

U.S. PATENT DOCUMENTS

| | | | | |
|---|---|---|---|---|
| 6,648,894 B2 * | 11/2003 | Abdelgany | ........... | A61F 2/4644 606/53 |
| 7,699,851 B2 * | 4/2010 | Dalton | ................ | A61B 17/15 606/87 |
| 7,736,366 B2 * | 6/2010 | Abdelgany | ........... | A61F 2/4644 606/86 R |
| 7,802,503 B2 * | 9/2010 | Couvillion | ............... | B26D 7/02 83/762 |
| 8,127,646 B2 * | 3/2012 | Couvillion | ............... | B26D 7/02 83/34 |
| 8,545,501 B2 * | 10/2013 | Wong | ..................... | A61B 17/56 606/86 R |
| 8,795,284 B2 * | 8/2014 | Ribeiro | .............. | A61B 17/1675 606/88 |
| 8,800,158 B1 * | 8/2014 | Shim | ..................... | A61F 2/4644 33/630 |

(Continued)

FOREIGN PATENT DOCUMENTS

| EP | 4483848 A2 * | 1/2025 | ......... | A61B 17/1604 |
|---|---|---|---|---|
| WO | WO-2012134819 A1 * | 10/2012 | ............. | A61B 17/14 |

(Continued)

*Primary Examiner* — Eric S Gibson
(74) *Attorney, Agent, or Firm* — Andrew F. Young, Esq; Nolte Lackenbach Siegel

(57) ABSTRACT

A bone cutting apparatus for holding a bone graft for shaping and sizing during surgery, including a polygonal cutting box having two opposing sides, at least one open side, and a base. The opposing sides have cutting slots, and a cutting accessory attaches to one of the opposing sides and has a central cutting slot that aligns with and expands the size of a cutting slot to pass a saw blade. A graft holding plate includes a platform with an upper surface to support a bone graft and further includes an underside with a pedestal configured to secure the holding plate to the base of the cutting box. The platform has a plurality of openings for passing screws into the bone graft. A top is placed on the opposing sides and includes downwardly oriented fenestration extensions configured for placement in the open sides and completes the enclosure for cutting.

10 Claims, 11 Drawing Sheets

(56) References Cited

U.S. PATENT DOCUMENTS

| | | | | |
|---|---|---|---|---|
| 9,173,665 B2* | 11/2015 | Couture | ............... | A61F 2/30942 |
| 9,700,438 B2* | 7/2017 | Kehres | .................... | B25B 5/163 |
| 12,102,546 B2* | 10/2024 | Settke | ................... | A61F 2/4644 |
| 2002/0082604 A1* | 6/2002 | Abdelgany | ............ | A61F 2/4644 |
| | | | | 623/16.11 |
| 2004/0034361 A1* | 2/2004 | Dalton | ................... | A61B 17/15 |
| | | | | 606/87 |
| 2004/0034362 A1* | 2/2004 | Abdelgany | ............ | A61F 2/4644 |
| | | | | 606/98 |
| 2004/0097946 A1* | 5/2004 | Dietzel | ................. | A61F 2/4644 |
| | | | | 606/79 |
| 2008/0011137 A1* | 1/2008 | Couvillion | ............... | B26D 7/02 |
| | | | | 83/78 |
| 2012/0253350 A1* | 10/2012 | Anthony | ................ | A61B 17/14 |
| | | | | 606/87 |
| 2013/0096680 A1* | 4/2013 | Ribeiro | ................. | A61F 2/4644 |
| | | | | 606/88 |
| 2015/0073419 A1* | 3/2015 | Couture | ................ | A61F 2/4081 |
| | | | | 606/87 |
| 2015/0297361 A1* | 10/2015 | Kehres | .................... | B25B 5/102 |
| | | | | 83/13 |
| 2023/0000646 A1* | 1/2023 | Settke | ................... | A61F 2/4644 |
| 2023/0097140 A1* | 3/2023 | Metcalfe | ................ | A61B 34/10 |
| | | | | 606/96 |
| 2023/0372123 A1* | 11/2023 | Jamali | .................... | A61F 2/4644 |
| 2025/0000523 A1* | 1/2025 | Cannon | ................ | A61L 27/3612 |
| 2025/0065527 A1* | 2/2025 | Cannon | ................ | A61F 2/30756 |

FOREIGN PATENT DOCUMENTS

| | | | | |
|---|---|---|---|---|
| WO | WO-2013055398 A1 * | 4/2013 | ......... | A61B 17/1675 |
| WO | WO-2021105495 A1 * | 6/2021 | ........... | A61F 2/4644 |

\* cited by examiner

BONE CUTTING SYSTEM AND APPARATUS

CROSS REFERENCES TO RELATED APPLICATIONS

The present application claims the benefit of U.S. Provisional Patent Application Ser. No. 63/365,146 filed May 23, 2022 (May 23, 2022), which application is incorporated in its entirety by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

BACKGROUND OF THE INVENTION

Field of the Invention: The present invention relates generally to methods of performing surgical bone transplants. More particularly, the present invention relates to methods and apparatus for securing and cutting donor allograft bone for fresh osteochondral allograft transplantation.

Background Discussion: Fresh osteochondral allograft transplantation has a long history of use in the treatment of joint disorders. One of the challenges of this procedure is the precise matching of the donor's bone to that of the recipient. The performance of this procedure depends on a generally equal sized donor joint surface to that of the recipient. This can be accomplished with a variety of imaging tools including calibrated radiographs, CT scans, or MRI scans. In treating large defects, the challenge is in achieving the appropriate thickness and orientation on the cut surface of the graft to avoid an excessively high joint surface and one that matches the angle of the patient's pre-injury joint surface. One final concern for surgeons performing this procedure is the precious nature of the graft. Not only are the grafts exceedingly rare and difficult to obtain, the cost of the grafts necessitates extreme care in protecting the graft from inadvertent loss from the surgical field during preparation. The present invention addresses these concerns through the use of a bone holding and cutting system.

BRIEF DESCRIPTION OF THE INVENTION

In its most essential aspect, the present invention is a bone holding apparatus and cutting system that includes a cutting box having a plurality of cutting slots. The box and slots are configured to accommodate a generally planar holding plate with multiple holes for placement of holding screws. The screws pass through the holding plate to secure a bone graft to a graft holding plate platform. The slots in the cutting box are spaced between 2 to 10 mm apart, and the cutting box further includes multiple apertures for the placement of wires or pins to hold the bone graft in a final cutting position after a desired orientation has been established. An adjustable positioning element in the base of the cutting box attaches to a pedestal under the holding plate and allows for fine adjustments of the position of the bone in all degrees of freedom (i.e., the six mechanical degrees of freedom). After the bone graft is positioned for cutting, a cutting box top is brought down onto the cutting box prior to cutting to contain cut material and to ensure that the bone cannot leave the surgical field during bone cutting.

BRIEF DESCRIPTION OF THE DRAWINGS

The invention will be better understood and objects other than those set forth above will become apparent when consideration is given to the following detailed description thereof. Such description makes reference to the annexed drawings wherein.

TERM KEY

Figure 1:
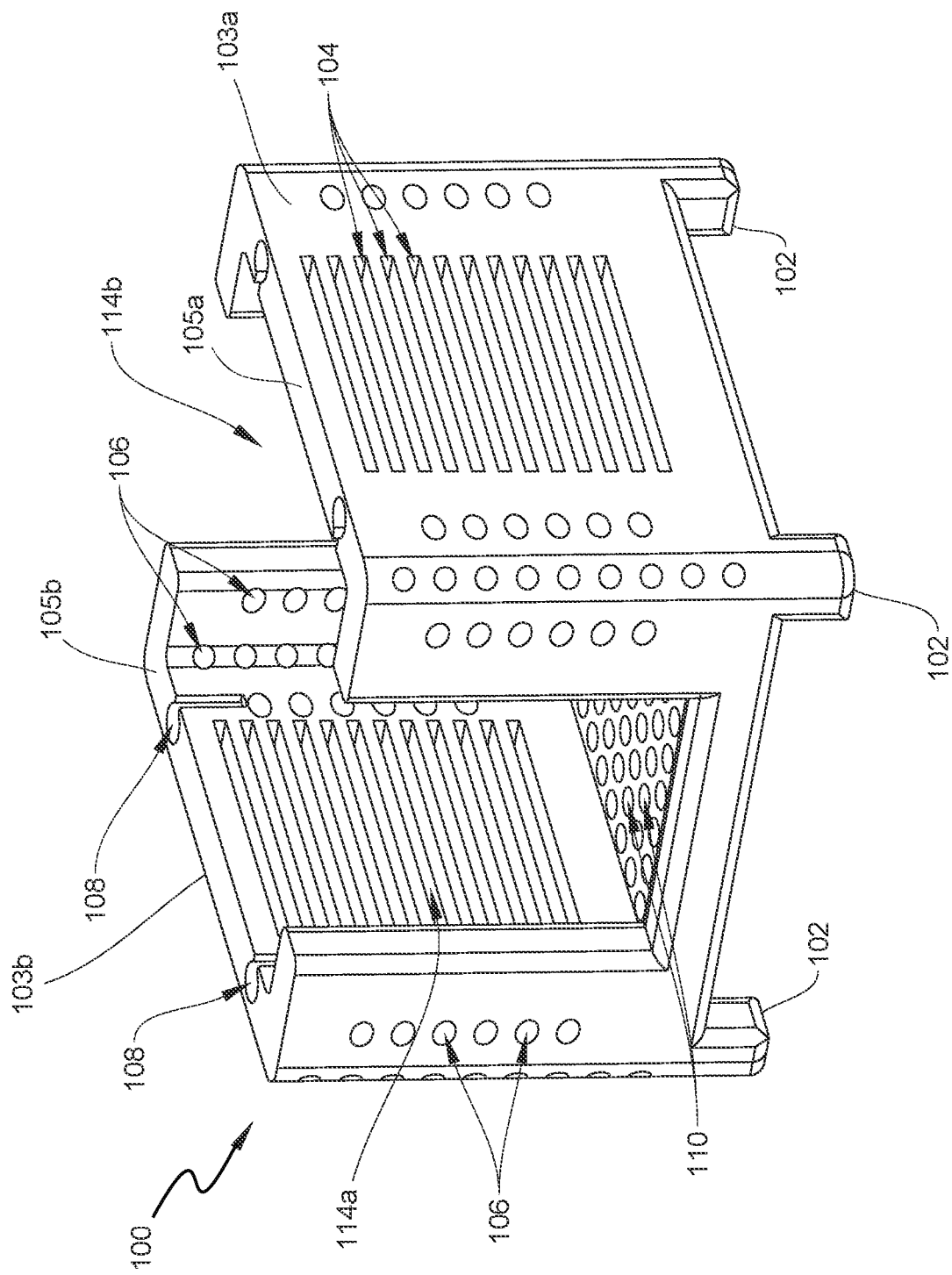
FIG. 1 is an upper front perspective view of the cutting box of the present invention.

100: cutting box
102: pedestals
103*a*/103*b*: opposing closed sides of cutting box
104: cutting slots
105*a*/105*b*: top surfaces of opposing sides
106: apertures
107: cutting box base
108: cavities
110: perforations
112: adjustable positioning element
114*a*/114*b*: front and rear cut-outs/windows
116: cutting accessory
117: cutting accessory face
118: extensions tongues
119: cutting accessory blade guide portion
120: central cutting slot
122: cutting box top
124: male extensions
125: underside/undersurface of cutting box top
126*a*/126*b*: fenestrated extensions
127: fenestrations
128: graft holding plate
129: platform (of graft holding plate)
130: perforations in platform
131: upper surface of platform
132: pedestal
134: bone graft
136: screws
138: locking pins

DETAILED DESCRIPTION OF THE INVENTION

Referring to FIGS. 1 through 11, wherein like reference numerals refer to like components in the various views, there is illustrated therein a new and improved bone cutting system and apparatus, generally denominated 100 herein.

FIG. 1 is a perspective view of the inventive bone cutting box 100 configured for use in the inventive bone cutting system. This view shows the box configured with a generally polygonal shape. The box preferably includes pedestals 102 to support the cutting box and to elevate it above the surgical field. The box is fabricated from autoclavable metal or plastic materials commonly used in surgery.

As clearly seen in the view, the cutting box contains opposing sides 103a, 103b having cutting slots 104 for the passage of a saw blade. Each opposing side is preferably U-shaped and wraps partially around and into an adjacent side. The cutting slots are spaced between 2 and 10 mm apart. The opposing sides of the cutting box each contain multiple through holes or apertures 106 from various angles to facilitate holding of the graft with pins and wires passed through the apertures to the box interior. The top surfaces 105a, 105b, respectively, of the opposing sides 103a, 103b of the cutting box each include between 1 and 10 female cavities 108 for accepting male elements (such as pegs, tabs, or posts) integral with a box top. The base 107 of the cutting box also preferably includes multiple perforations 110 to facilitate visualization of the graft from below as well as for fixation of the adjustable positioning element 112. A window or cut-out is formed on either side or two opposing open sides of the box—e.g., front and rear windows, respectively, 114a, 114b—for adjustment and manipulation of the graft during pinning and prior to placement of the cutting box top 122 and the subsequent cutting of the graft. The windows effectively create a through passage traversing the cutting box and provide openings for the placement and positioning of fenestrated extensions, described more fully below.

Figure 2:
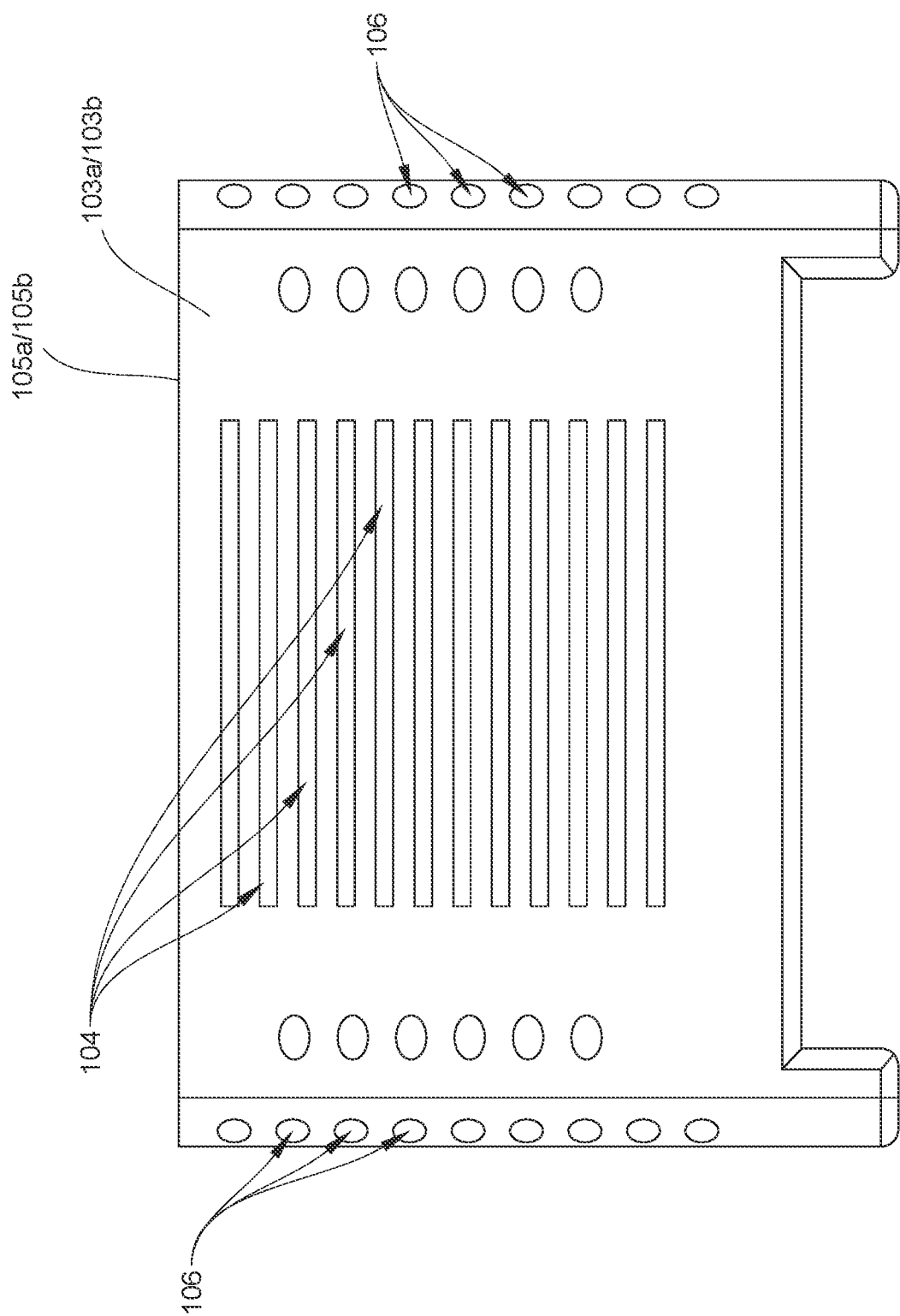
FIG. 2 is a right side view in elevation thereof, the left side view in elevation being a mirror image thereof.

FIG. 2 is a side view in elevation of the cutting box cutting outer side showing multiple spaced-apart elongate cutting slots 104 disposed through the cutting box sides 103a, 103b, at intervals of between 2 and 10 mm apart and having a width sufficient to allow passage of a cutting blade of a bone saw. Multiple apertures 106 for fixation of the graft are shown at both sides (i.e., outboard of the ends) of the cutting slots.

Figure 3:
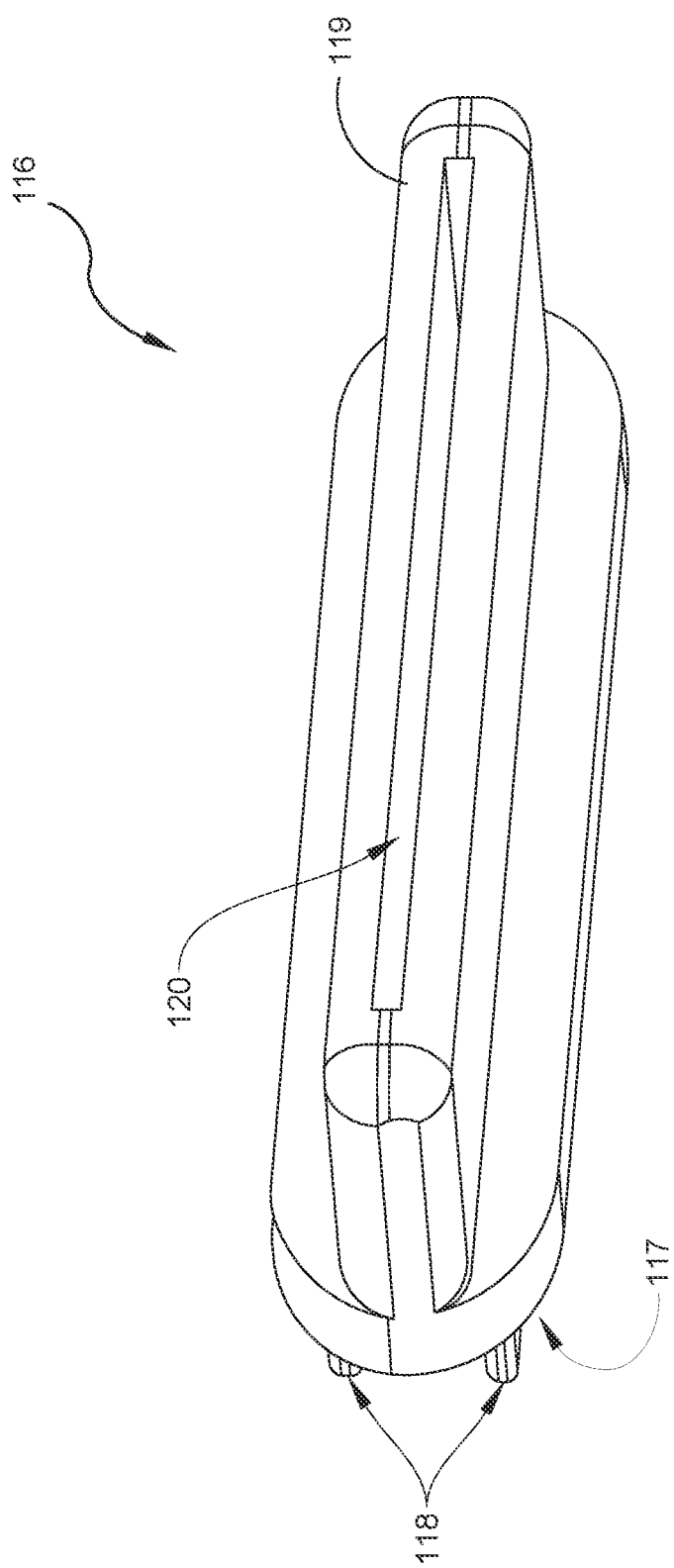
FIG. 3 is a lower front perspective view of the cutting accessory.

FIG. 3 is a cutting accessory 116 shown in perspective view. This accessory includes a planar face 117 having extension tongues 118 configured and spaced apart at a distance to insert into two of the cutting slots of the cutting box (preferably adjacent slots) so as to securely hold the face of the cutting accessory against the side of the cutting box. It also includes a blade guide portion 119 with a central cutting slot 120. When this accessory is installed on the cutting box outer surface by placing the two extension tongues 118 into adjacent cutting slots (i.e., straddling, or above and below), respectively, the desired cutting slot, the central cutting slot 120 aligns with and acts as an extension of the cutting slot of the box, thereby ensuring a flat and smooth cut on the bone graft.

Figure 4:
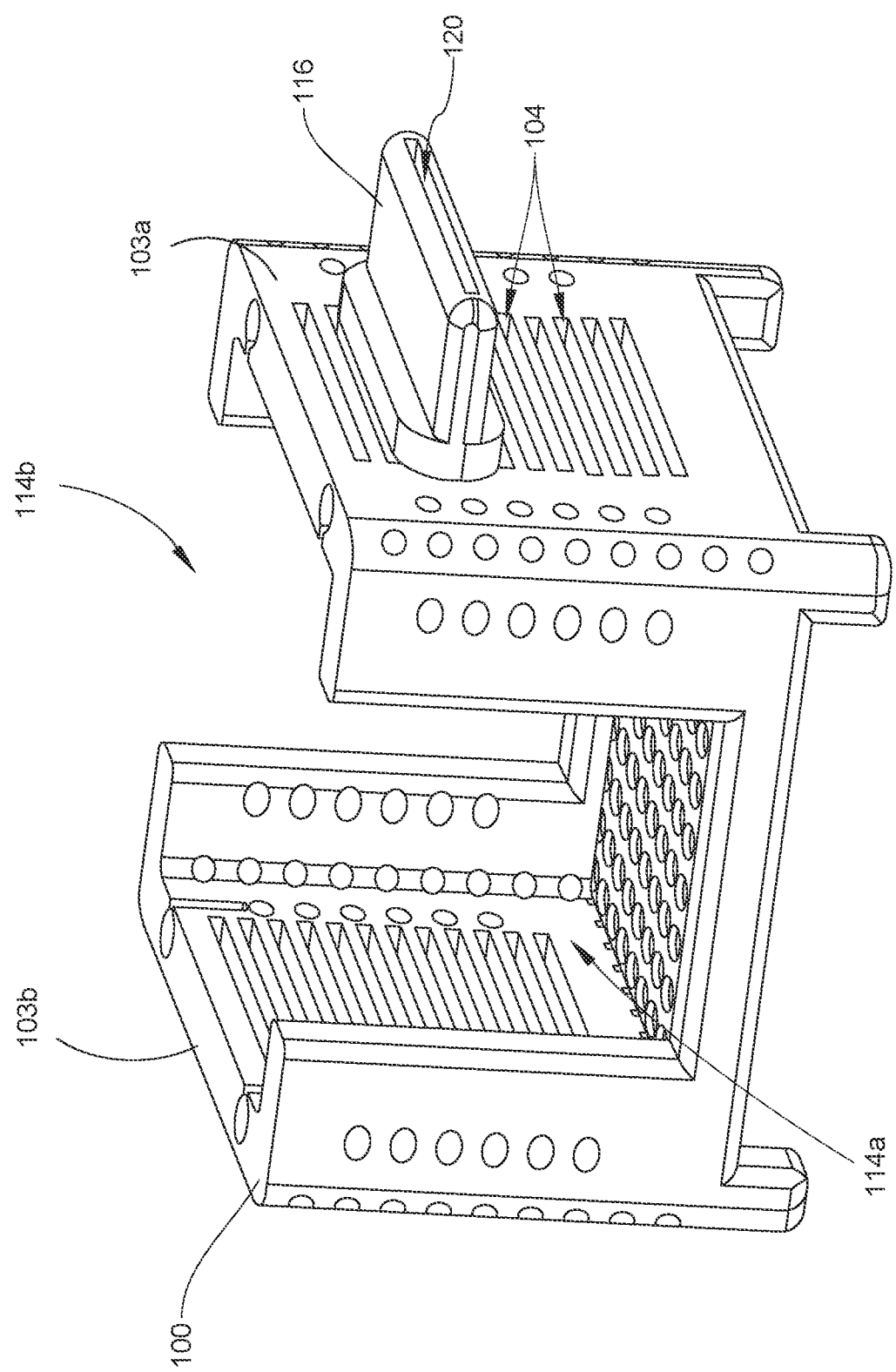
FIG. 4 is an upper perspective view of the cutting box with the cutting accessory of FIG. 3 shown attached.

FIG. 4 is a perspective view of the cutting box 100 with the cutting accessory 116 and its tongue extensions 118 (not shown) placed into the cutting slots 104 (cutting slots actually for cutting accessory installation not shown) above and below the desired cut slot.

Figure 5:
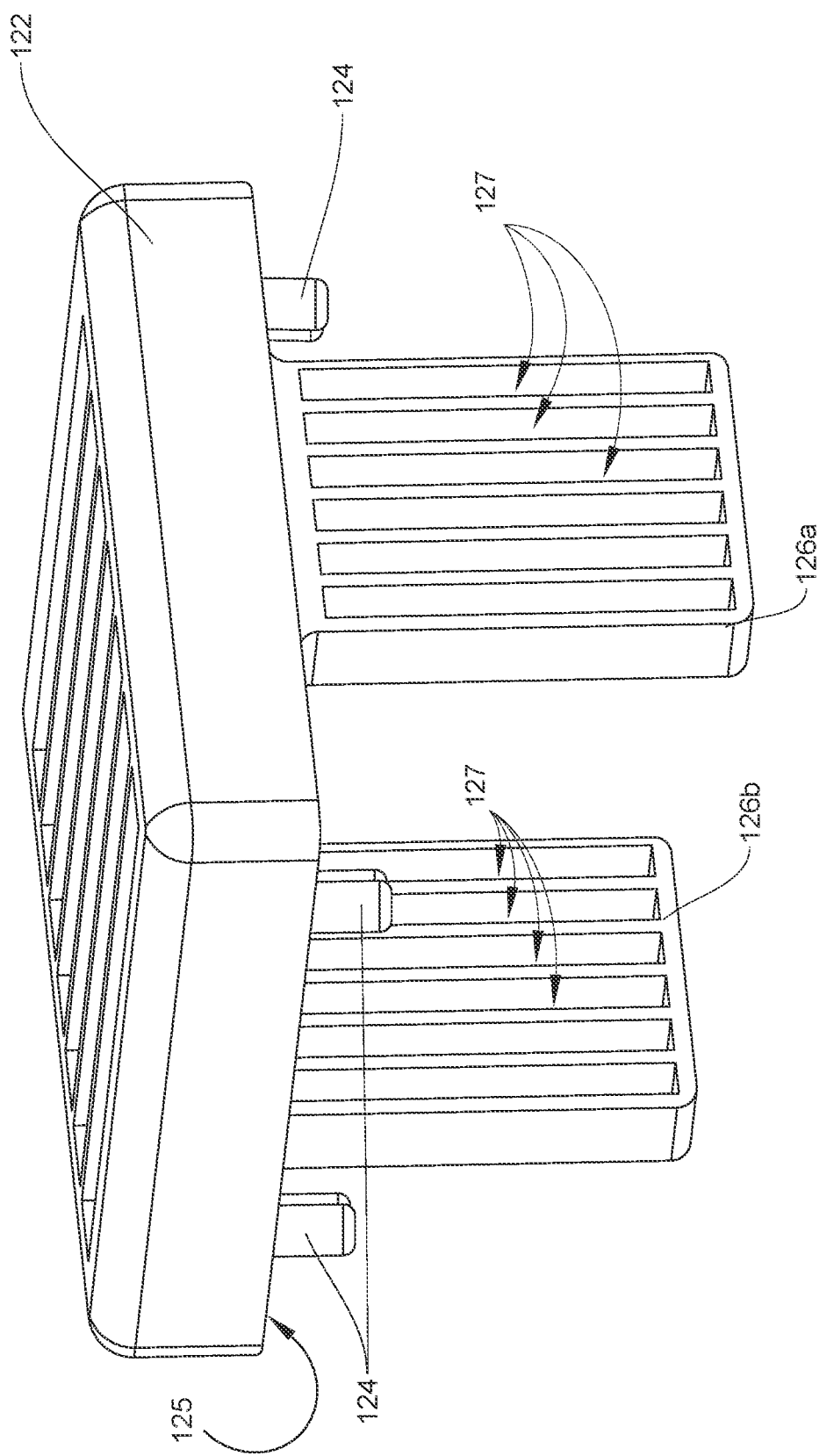
FIG. 5 is a perspective view of the cutting box top.

FIG. 5 is a perspective view of the cutting box top 122. As can be seen in the view, the top features four male extensions (pins or posts) 124 extending from the undersurface 125 of the top and mating with the female cavities 108 of the cutting box (not shown) to achieve a stable placement of the top on the cutting box. The top also contains at least one, and preferably two, downwardly-oriented fenestrated extensions 126a, 126b, to control the graft in the event of movement near the end of a cut. The extensions also effectively complete the enclosure, making the box's interior space accessible while having six material sides. The vertically oriented fenestrations 127 facilitate visualization of the graft during the cut and provide access for a vertical cut, if needed. If only one extension is fenestrated, the other may be solid and thus constitute a complete barrier to flying bone fragments and dust.

Figure 6:
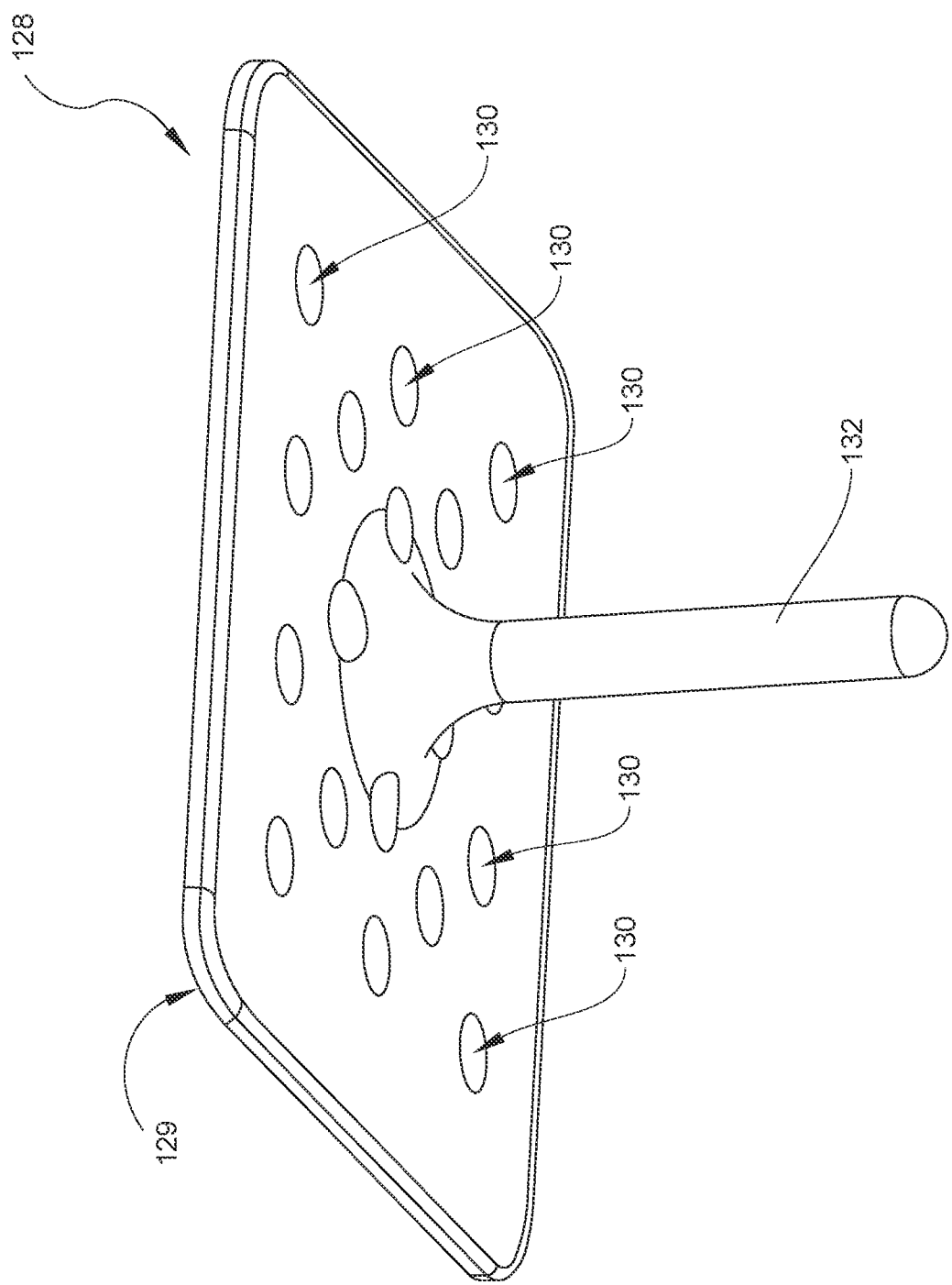
FIG. 6 is a lower perspective view of the graft holding plate.

FIG. 6 is an inferior perspective view of the graft holding plate 128. The graft holding plate 128 is fabricated from metal and includes a platform 129 having multiple perforations 130 for attachment of the graft to the upper surface 131 of the platform 129 using bone screws (not shown in this view; but see FIG. 8). The plate then facilitates fine manipulation of the graft in the cutting box and minimizes the risk of the graft slipping from the surgical field. In this rendition of the invention a single pedestal 132 extends downwardly from the plate.

Figure 7:
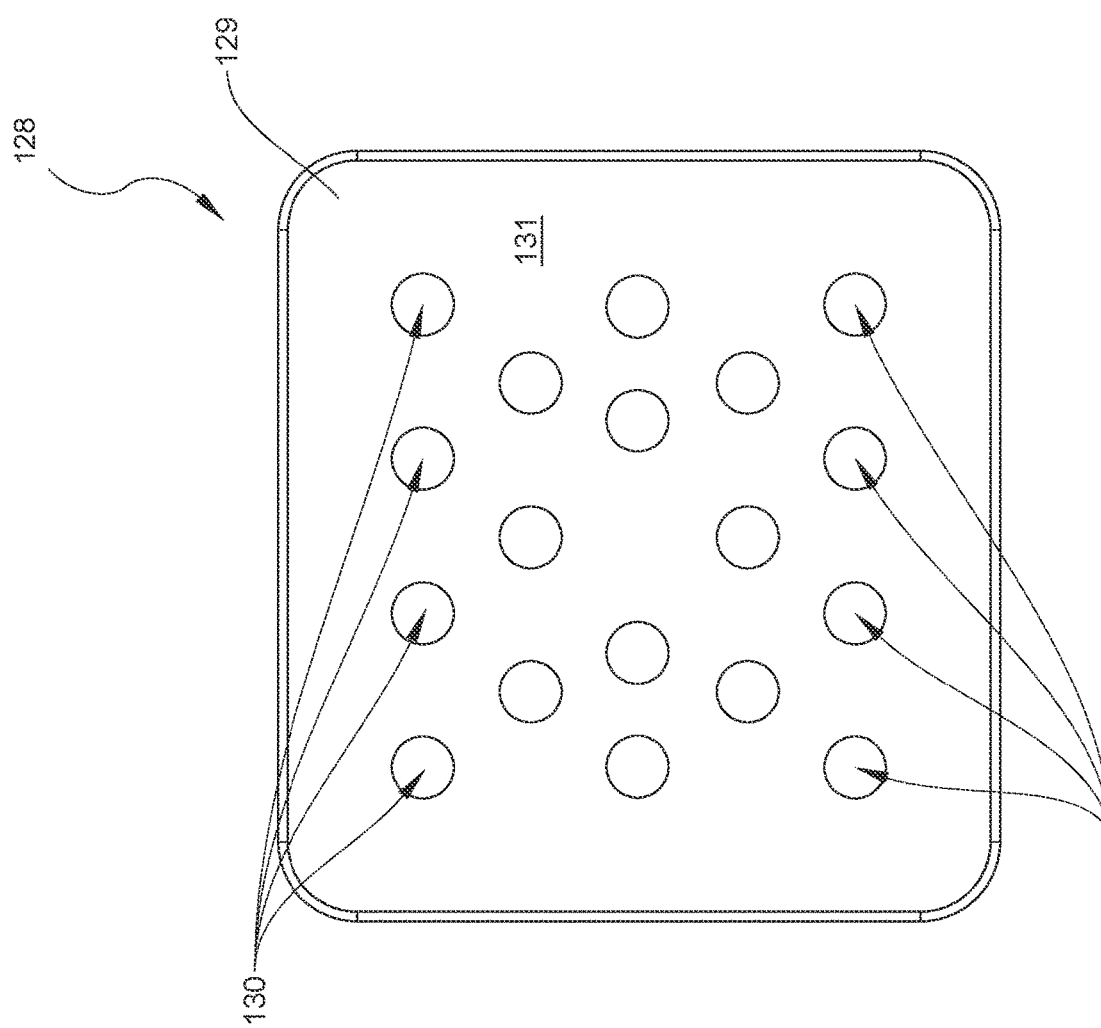
FIG. 7 is a top plan view of the graft holding plate.

FIG. 7 is a top plan view of the graft holding plate 128, showing that the plate's platform 129 may include a generally planar upper surface 131, and the platform may include multiple perforations 130 for passing screws to hold the bone graft. In some embodiments, the upper surface may be configured or contoured to fit the intended orthopedic procedure.

Figure 8:
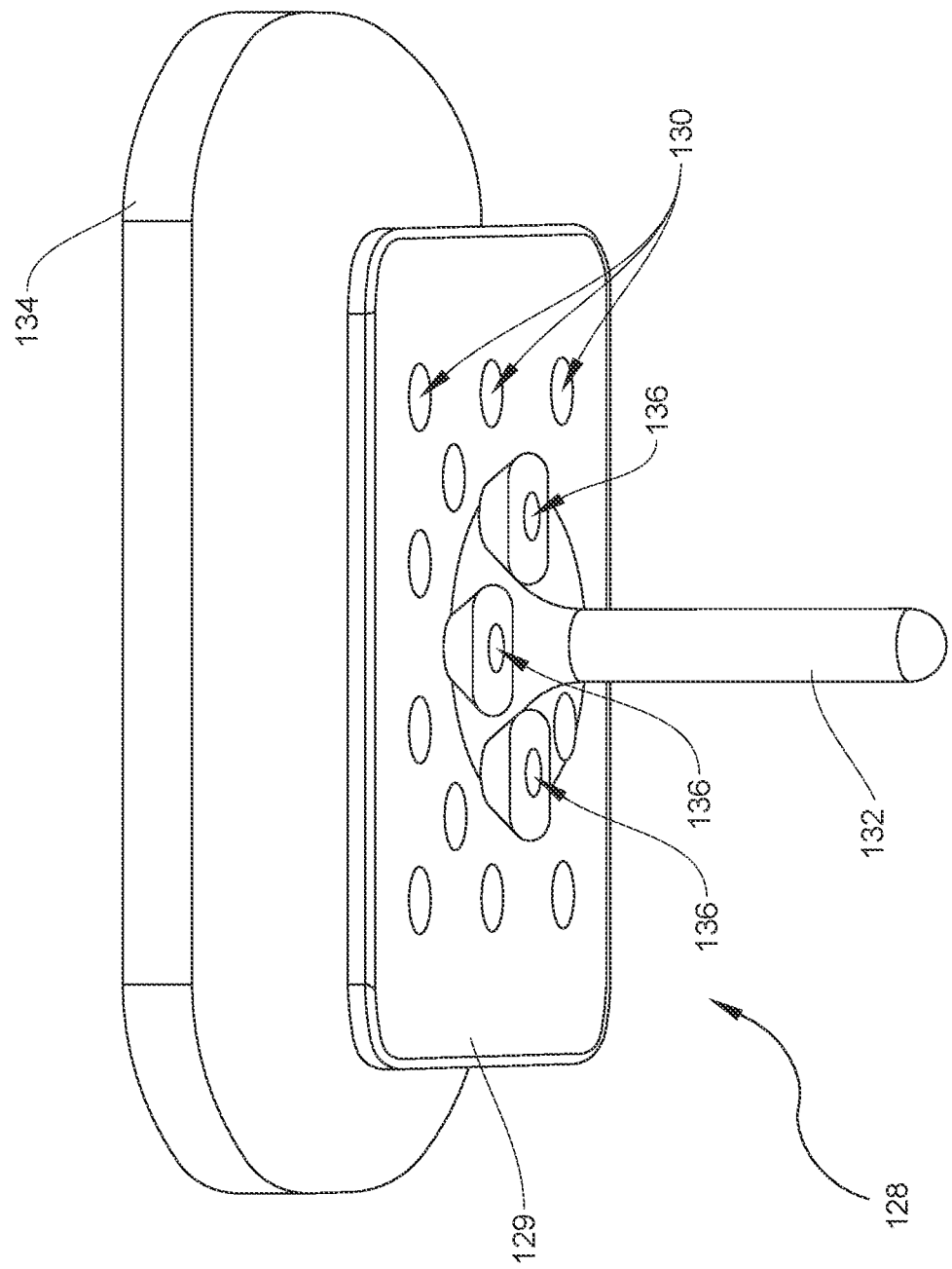
FIG. 8 is a lower inferior perspective view of the graft holding plate shown with a bone graft attached to the graft holding plate.

FIG. 8 is an inferior perspective view showing the graft holding plate 128 supporting and securing a bone graft 134 with three (3) screws 136 passing through the perforations 130 in the platform 129 and into the bone graft 134. A single pedestal 132 extends downwardly from the platform. In an alternative embodiment, multiple pedestals can extend downwardly into a holding element.

Figure 9:
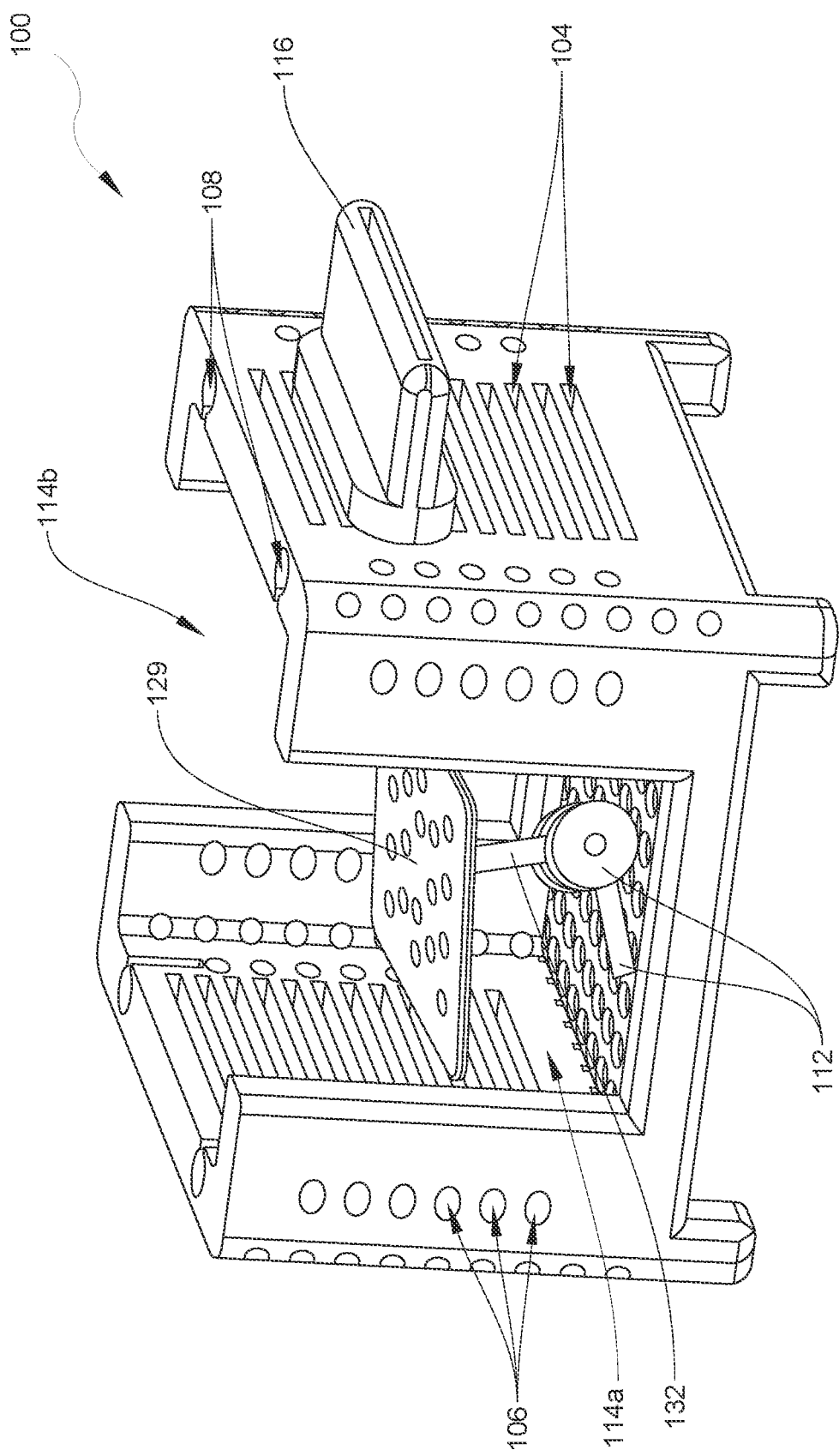
FIG. 9 is an upper perspective view showing the cutting box with the cutting accessory installed on a side and the graft holding plate installed in the box interior.

FIG. 9 is perspective view of the cutting box 100 and cutting accessory 116 as shown in FIG. 6 with the additional placement of an adjustable positioning element 112, which further stabilizes the graft holding plate 128 to the base of the cutting box 100 using the pedestal 132. By loosening the screw on the adjustable positioning element 112, the plate can be moved and adjusted in all mechanical degrees of freedom such that the bone graft is adjusted to the desired position prior to final pinning of the bone through the apertures 106 in the box.

Figure 10:
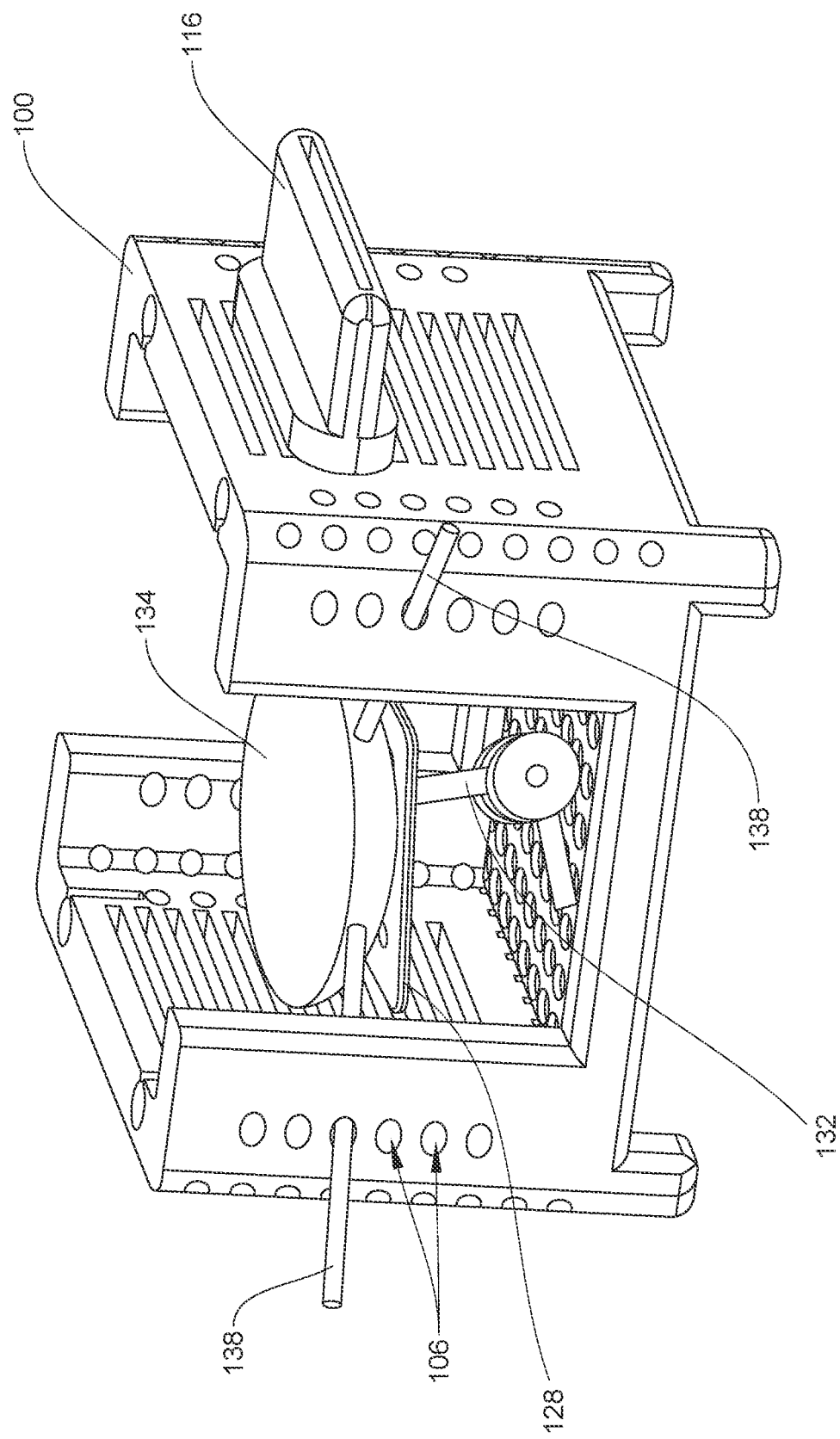
FIG. 10 is the same view with a bone graft secured to the graft holding plate.
Figure 11:
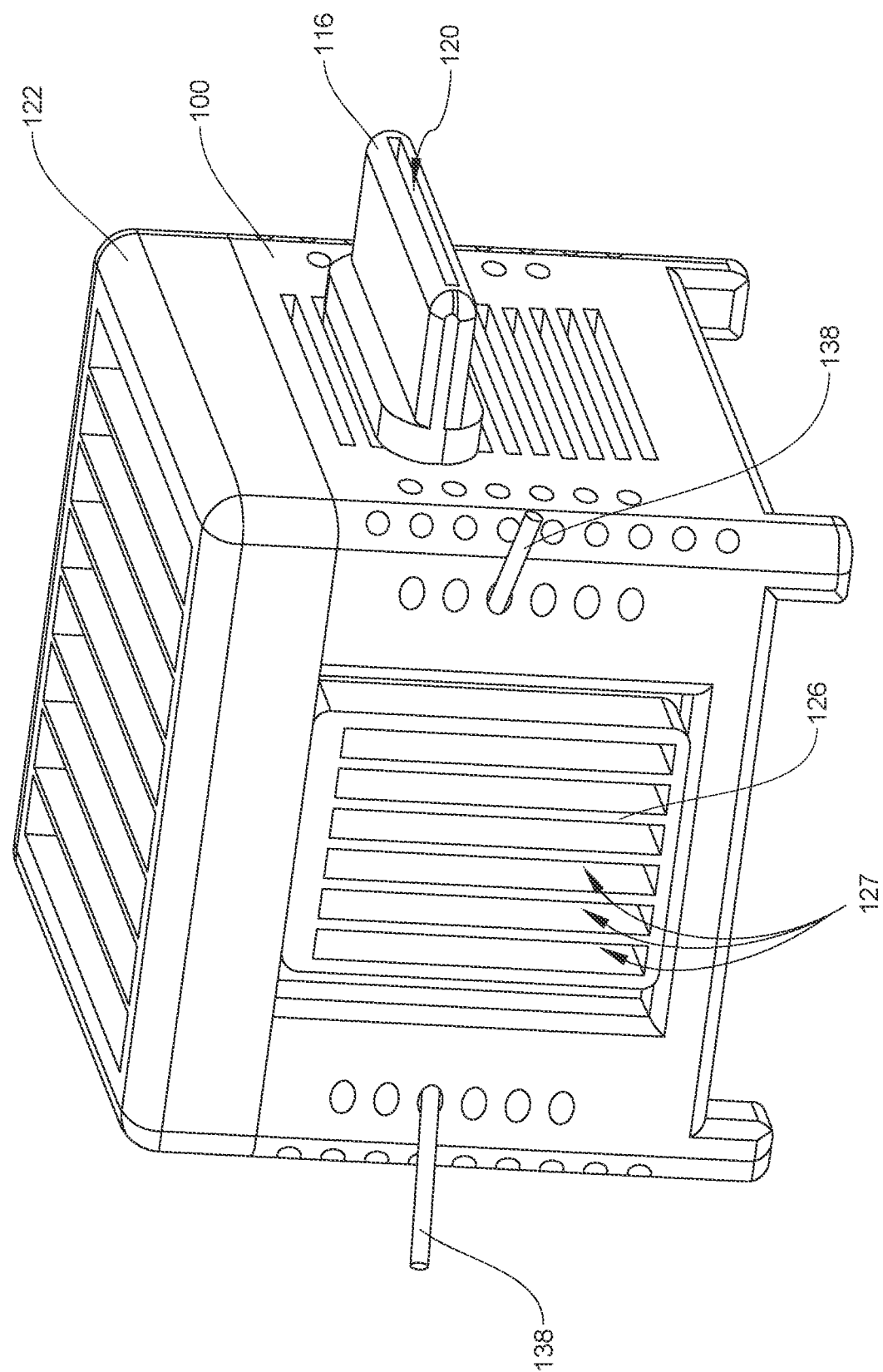
FIG. 11 is a perspective view of the cutting box shown with the cutting box top, cutting accessory, and fenestrated extensions installed.

FIG. 10 is a perspective view of the cutting box 100 and cutting accessory 116 shown in FIG. 11 with a bone graft 134, in this case (somewhat schematically) a patella, fixed to the plate after final adjustment of the position and placement of locking pins 138 passing through the apertures 106 in the cutting box.

FIG. 11 is a perspective view of the cutting box 100 shown in FIG. 12 with the cutting box top 122 installed prior to final graft cutting through the cutting accessory 116. The graft is held fixed in plate through the use of the graft holding plate 128 (not shown) and the locking pins (or cross pins) 138. The downwardly directed fenestrated extensions 126 from the cutting box top 122 allow visualization of the graft during the cut through the vertically oriented fenestrations 127.

As will be appreciated, in use there are infinite degrees of freedom in positioning the bone graft for cutting using the graft holding plate 128, as seen in FIG. 6, until the point in the procedure at which the bone is pinned in place with the locking pins 138. The principle and purpose are to enable fine tuning of the bone alignment first and then securely holding that alignment with multiple locking pins 138. The saw cut for such transplant procedures must be perfect, not only in direction in all three dimensions, but it must also be at the correct depth to match the bone taken from the patient. This ensures that the height of the bone and the joint surface are restored in the transplant patient. This is achieved by using the graft holder to change the position and orientation of the bone until it is optimized, at which time it is pinned in place.

Multiple slots from multiple directions provides the surgeon the ability to gauge the depth of the cut all around the bone to be cut and then to enable a cut to be made from different directions. This is a practical solution to limitations in the performance of many bone saw blades, firstly owing to their length (i.e., not being long enough to span and traverse the entire width of the cutting box), and secondly owing to the fact that the deeper they cut, the more they tend to skive or bend.

The above disclosure is sufficient to enable one of ordinary skill in the art to practice the invention, and it provides the best mode of practicing the invention presently contemplated by the inventor. While this is a full and complete disclosure of the preferred embodiments of this invention, it does not limit the invention to the exact construction, dimensional relationships, and operation shown and described, whether stated explicitly or implicitly. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A bone cutting system and apparatus for holding a harvested bone graft for shaping and sizing for placement in a transplant site during surgery, the system and apparatus comprising:
    a cutting box configured with a generally polygonal shape and having two opposing sides, at least one open side, and a base, said opposing sides having a plurality of elongate cutting slots for passage of a saw blade;
    a cutting accessory having extension tongues spaced and configured for insertion in two or more of said cutting slots of said opposing sides of said cutting box, said cutting accessory having a central cutting slot that aligns with and extends one cutting slot when installed on one of said opposing sides of said cutting box to facilitate a flat and smooth cut on a bone graft;
    a graft holding plate having a platform with an upper surface for supporting a bone graft and an underside with a downwardly oriented pedestal configured to secure to said base of said cutting box, said platform having a plurality of openings for use in securing the bone graft to said platform;
    a top configured for placement atop said opposing sides; and
    at least one fenestrated extension configured for placement in said at least one open side between said top and said base of said cutting box.

2. The bone cutting system and apparatus of claim 1, wherein said cutting box, said graft holding plate, said top, and said at least one fenestrated extension are each fabricated from autoclavable materials.

3. The bone cutting system and apparatus of claim 1, wherein said plurality of elongate cutting slots on said opposing sides are spaced between 2 and 10 mm apart.

4. The bone cutting system and apparatus of claim 1, including two fenestrated extensions.

5. The bone cutting system and apparatus of claim 4, wherein said fenestrated extensions include a plurality of vertically-oriented slots.

6. The bone cutting system and apparatus of claim 1, wherein said at least one fenestrated extension includes a plurality of vertically-oriented slots.

7. The bone cutting system and apparatus of claim 1, wherein said upper surface of said platform of said graft holding plate is generally planar.

8. The bone cutting system and apparatus of claim 1, wherein each of said opposing sides of said bone cutting box have a top with a plurality of female openings, and said top has an underside with male elements configured for insertion into said female openings in said two opposing sides.

9. The bone cutting system and apparatus of claim 1, wherein said graft holding plate has all mechanical degrees of freedom until a bone supported on and secured to said platform is locked in place with one or more locking pins.

10. A bone cutting apparatus, comprising:
    a bone cutting box having opposing right and left sides, each having a plurality of spaced apart horizontally oriented slots and a top surface and a plurality of apertures for passage of locking pins, front and rear open sides, and a base with a plurality of apertures for secure insertion of a pedestal;
    a top configured for secure attachment to said top surface of said opposing right and left sides and further configured with one or more downwardly-depending fenestrated extensions which create a complete enclosure when said top is secured to said right and left sides of said bone cutting box;
    a cutting accessory having a cutting slot sized substantially the same as the horizontally oriented slots in said right and left sides and configured for installation on one of said right and left sides to bring said cutting slot into alignment with one of said horizontally oriented slots so as to extend depth of one of said horizontally oriented slots;
    a graft holding plate including a platform for supporting and securing a bone graft and a pedestal configured for insertion into one of said apertures in said base of said bone cutting box; and
    locking pins for insertion through said plurality of apertures in said right and left sides and threadable insertion into bone.

* * * * *